United States Patent
Da Silva et al.

(10) Patent No.: US 10,149,631 B2
(45) Date of Patent: Dec. 11, 2018

(54) STRUCTURAL HEALTH MONITORING SENSORY SYSTEM INTEGRATED TO A SELF-ADAPTING MORPHING SYSTEM

(71) Applicant: Embraer S.A., São José dos Campos-SP (BR)

(72) Inventors: Paulo Anchieta Da Silva, São José dos Campos (BR); Tomaz Lazanha, São José dos Campos (BR); Ricardo Pinheiro Rulli, São José dos Campos (BR); Fernando Dotta, São José dos Campos (BR)

(73) Assignee: Embraer S.A., São José dos Campos (BR)

( * ) Notice: Subject to any disclaimer, the term of this patent is extended or adjusted under 35 U.S.C. 154(b) by 49 days.

(21) Appl. No.: 14/808,142

(22) Filed: Jul. 24, 2015

(65) Prior Publication Data

US 2017/0021918 A1    Jan. 26, 2017

(51) Int. Cl.
| | |
|---|---|
| *A61B 5/053* | (2006.01) |
| *G01M 99/00* | (2011.01) |
| *G01M 5/00* | (2006.01) |
| *B64F 5/60* | (2017.01) |
| *B64C 23/06* | (2006.01) |
| *B64C 3/44* | (2006.01) |
| *B64D 45/00* | (2006.01) |

(Continued)

(52) U.S. Cl.
CPC ............ *A61B 5/053* (2013.01); *B64C 23/072* (2017.05); *B64F 5/60* (2017.01); *G01M 5/0016* (2013.01); *G01M 5/0033* (2013.01); *G01M 5/0041* (2013.01); *G01M 99/00* (2013.01); *B64C 2003/445* (2013.01); *B64C 2003/543* (2013.01); *B64D 2045/0085* (2013.01); *F03D 7/022* (2013.01); *F05B 2240/31* (2013.01); *Y02T 50/164* (2013.01)

(58) Field of Classification Search
CPC combination set(s) only.
See application file for complete search history.

(56) References Cited

U.S. PATENT DOCUMENTS 6,006,163 A * 12/1999 Lichtenwalner ......... G01H 5/00
702/34
8,788,122 B1    7/2014 Sankrithi et al.
(Continued)

FOREIGN PATENT DOCUMENTS

| WO | 2005/066244 A2 | 7/2005 |
| WO | 2009/002586 A2 | 12/2008 |

OTHER PUBLICATIONS

International Search Report dated Nov. 9, 2016, issued in corresponding International Application No. PCT/BR2016/000070.
(Continued)

*Primary Examiner* — Thomas G Black
*Assistant Examiner* — Ana D Thomas
(74) *Attorney, Agent, or Firm* — Nixon & Vanderhye P.C.

(57) ABSTRACT

A system and method for damage detection and for evaluating the real operation conditions for structural platforms using structural health monitoring is integrated to a system and method that permits for the platform to provide a flexible geometric control considering a self-adapting morphing which is capable of providing better operating structural platform performance.

20 Claims, 9 Drawing Sheets

Example of the structural integrity management system evaluation and self-adapting morphing process

(51) Int. Cl.
*B64C 3/54* (2006.01)
*F03D 7/02* (2006.01)

(56) References Cited

U.S. PATENT DOCUMENTS

| | | | | |
|---|---|---|---|---|
| 2003/0009300 | A1* | 1/2003 | Giurgiutiu | G01N 29/11 702/35 |
| 2008/0255781 | A1* | 10/2008 | Beard | G01N 29/041 702/59 |
| 2008/0308683 | A1* | 12/2008 | Sankrithi | B64C 23/076 244/199.4 |
| 2010/0119704 | A1* | 5/2010 | Hemmelgarn | B29C 35/0272 427/140 |
| 2011/0084174 | A1* | 4/2011 | Hemmelgarn | B64C 3/48 244/200 |
| 2011/0163205 | A1* | 7/2011 | Shepshelovich | B64C 3/14 244/219 |
| 2014/0306067 | A1* | 10/2014 | Guida | B64C 23/065 |
| 2015/0168353 | A1* | 6/2015 | Gallo | G01N 29/09 702/39 |
| 2015/0369723 | A1* | 12/2015 | Da Silva | G01N 21/17 427/140 |
| 2016/0340058 | A1 | 11/2016 | Da Silva et al. | |

OTHER PUBLICATIONS

Written Opinion of the International Searching Authority dated Nov. 9, 2016, issued in corresponding International Application No. PCT/BR2016/000070.

Mieloszyk, M., et al., "Application of fibre Bragg grating sensors for structural health monitoring of an adaptive wing," Smart Materials ad Structures, vol. 20, No. 12, Nov. 2011, XP020214592, Abstract.

Murphy, Erin B., et al., "The world of smart healable materials," Progress in Polymer Science, vol. 35, Nos. 1-2, Jan. 2010, XP026852569, Abstract.

* cited by examiner

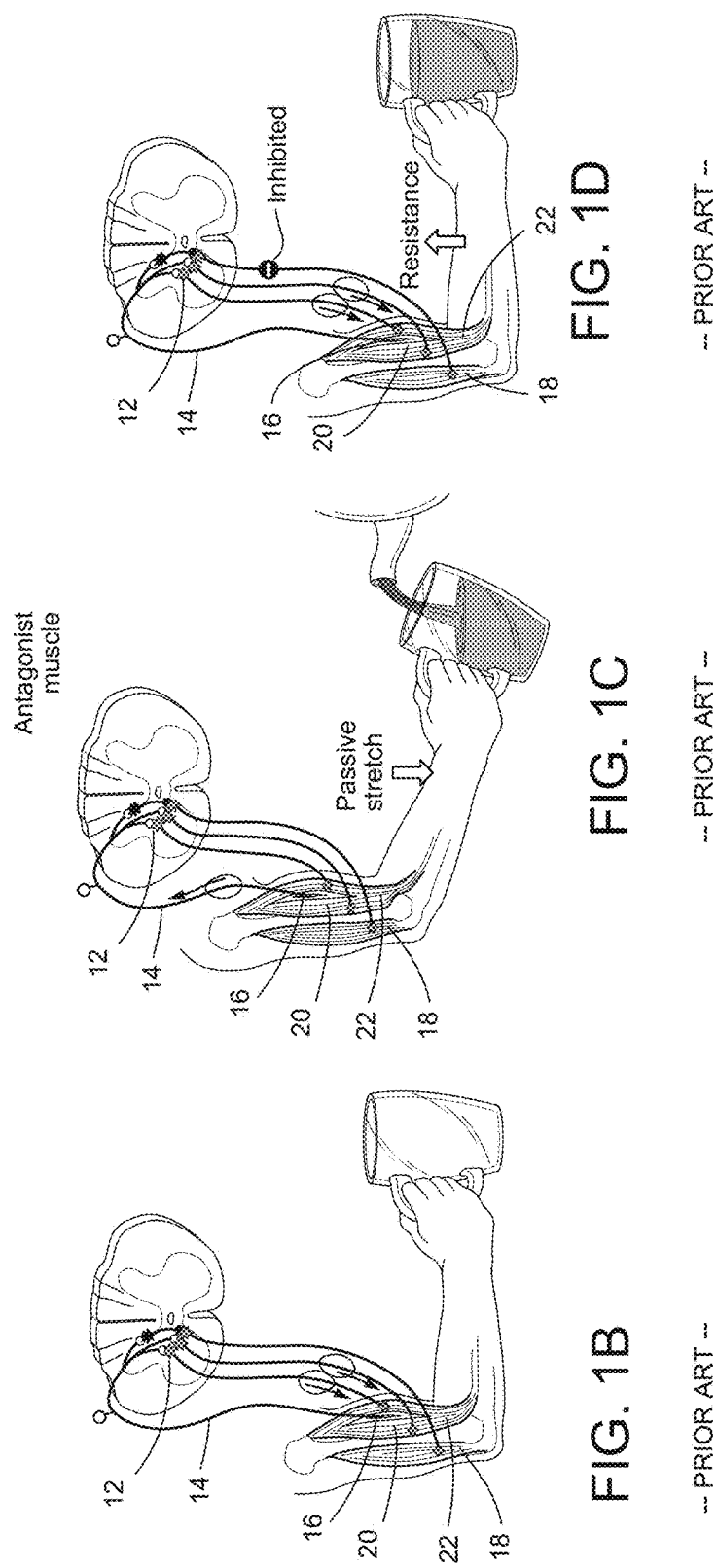

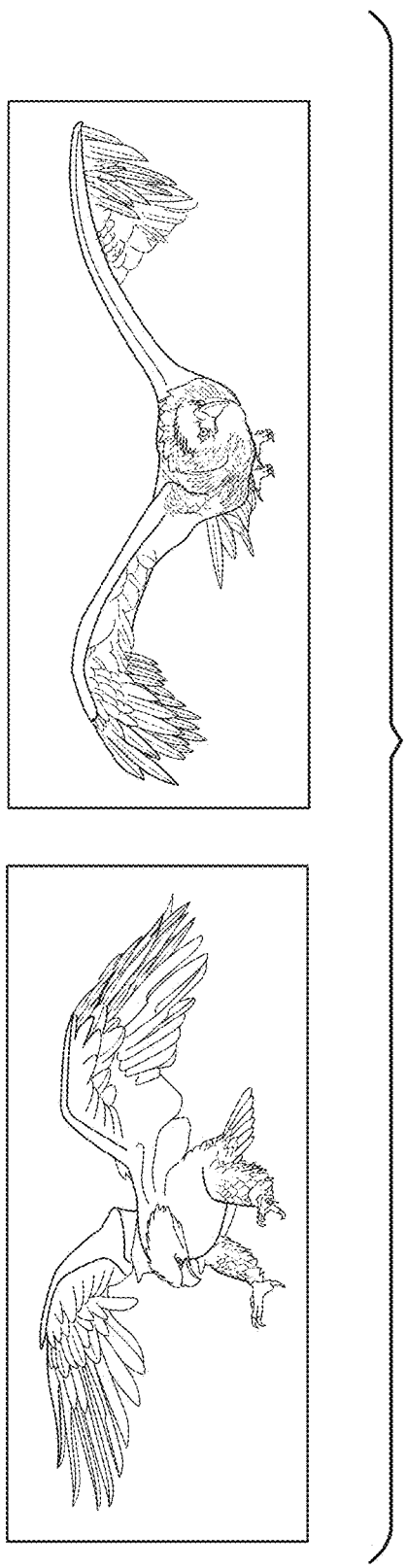
FIG. 2 Adaptive morphology of a wing
-- PRIOR ART --

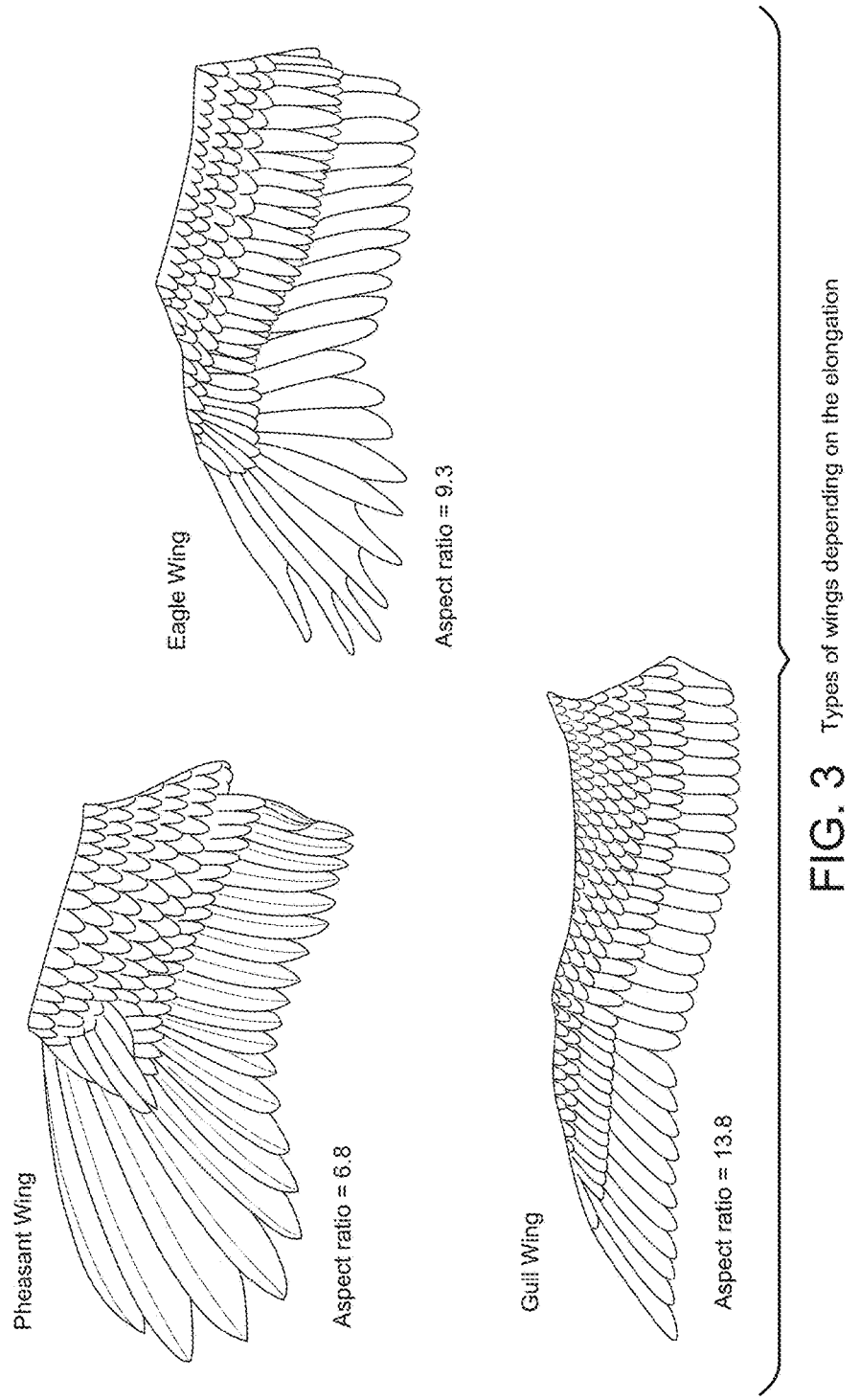
FIG. 3  Types of wings depending on the elongation
-- PRIOR ART --

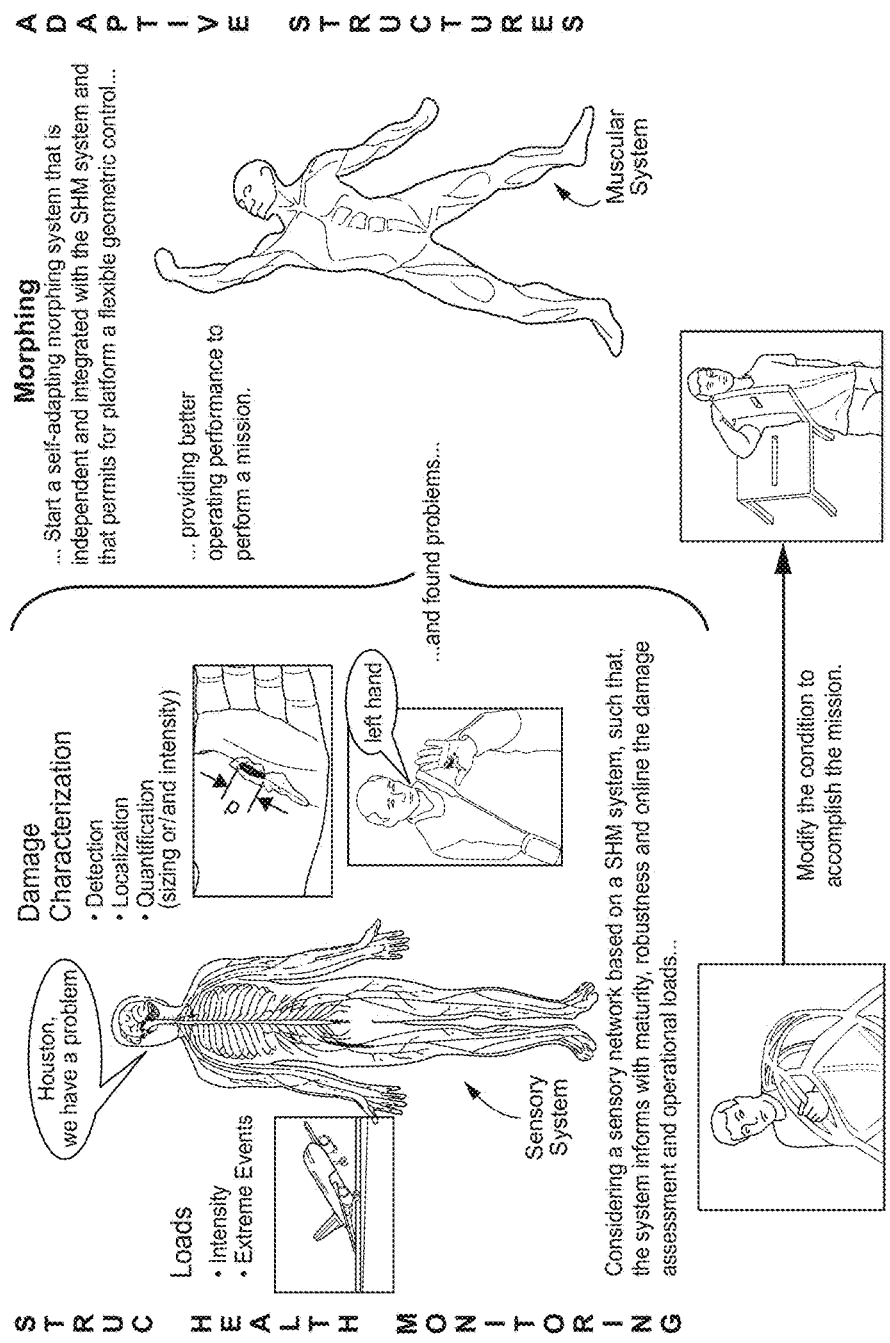
FIG. 4  SHM system (resembling the human nervous system) integrated with the SAM (resembling the human muscular system)
-- PRIOR ART --

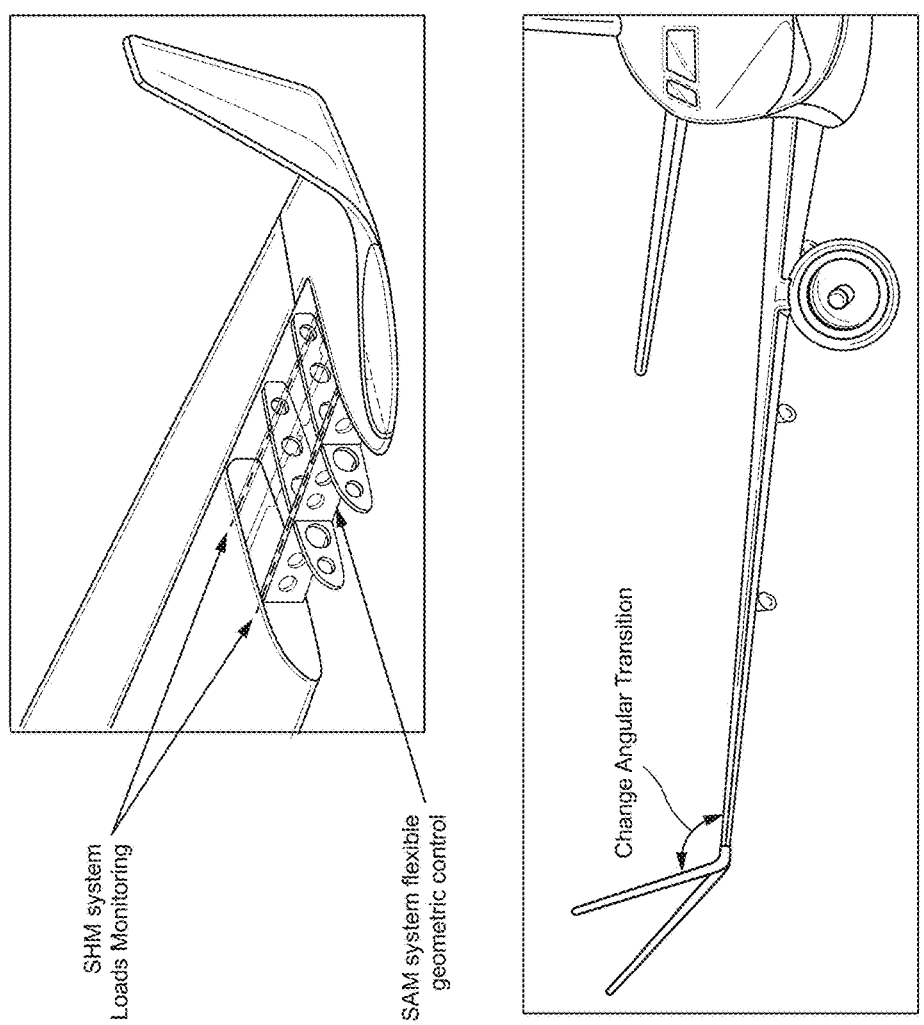

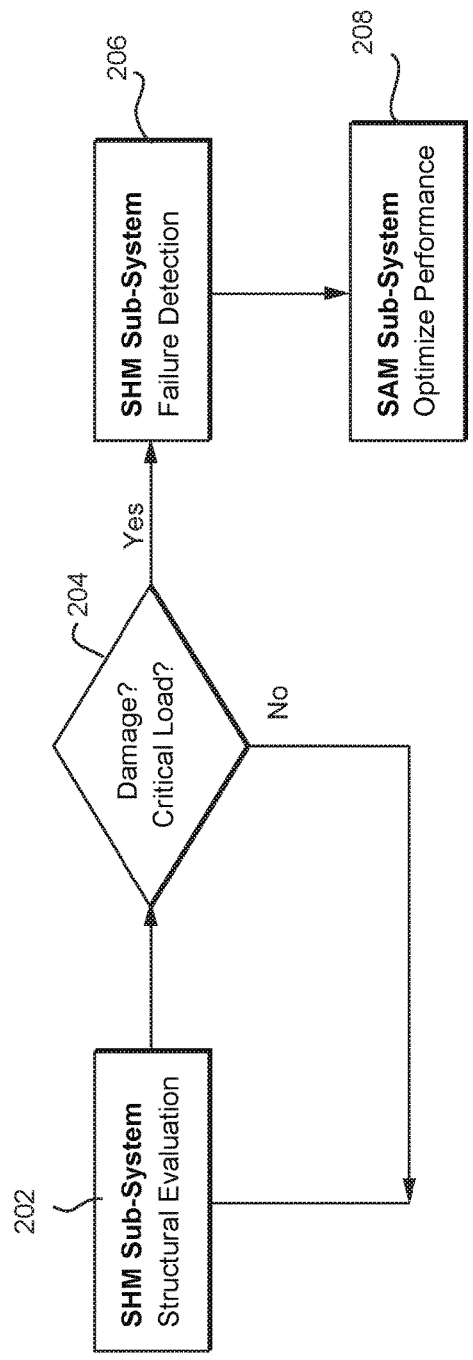
FIG. 6A  Example of the structural integrity management system evaluation and self-adapting morphing process

STRUCTURAL HEALTH MONITORING SENSORY SYSTEM INTEGRATED TO A SELF-ADAPTING MORPHING SYSTEM

CROSS-REFERENCE TO RELATED APPLICATIONS

None.

STATEMENT REGARDING FEDERALLY SPONSORED RESEARCH OR DEVELOPMENT

None.

FIELD

The technologies herein relate to structural health monitoring (herein called "SHM") including sensor systems that automatically calculate operational loads and detect damage to structures including but not limited to aircraft, and to such sensor systems related to smart materials with capabilities of performing self-adapting morphing ("SAM") in monitored structures.

BACKGROUND AND SUMMARY

A system and method for damage detection and for evaluating real operation conditions for structural platforms using structural health monitoring is integrated into a system and method that permits the platform to provide a flexible geometric control considering a self-adapting morphing which is capable of providing better operating structural platform performance.

BRIEF DESCRIPTION OF THE DRAWINGS

The following detailed description of exemplary non-limiting illustrative embodiments is to be read in conjunction with the drawings of which:

FIGS. 1A-1D shows human integrated system comprising nervous and muscular systems realizing a mission;

FIG. 2 shows different example morphologies of a wing;

FIG. 3 shows types of wings with different elongation;

FIG. 4 shows an example non-limiting SHM system (resembling the human nervous system) integrated with the SAM (resembling the human muscular system);

FIG. 5 shows an example non-limiting aircraft load monitoring and morphing by a SHM sub-system integrated with a SAM sub-system;

FIG. 6A shows an example structural integrity management system evaluation and self-adapting morphing process;

DETAILED DESCRIPTION

Figure 1A:
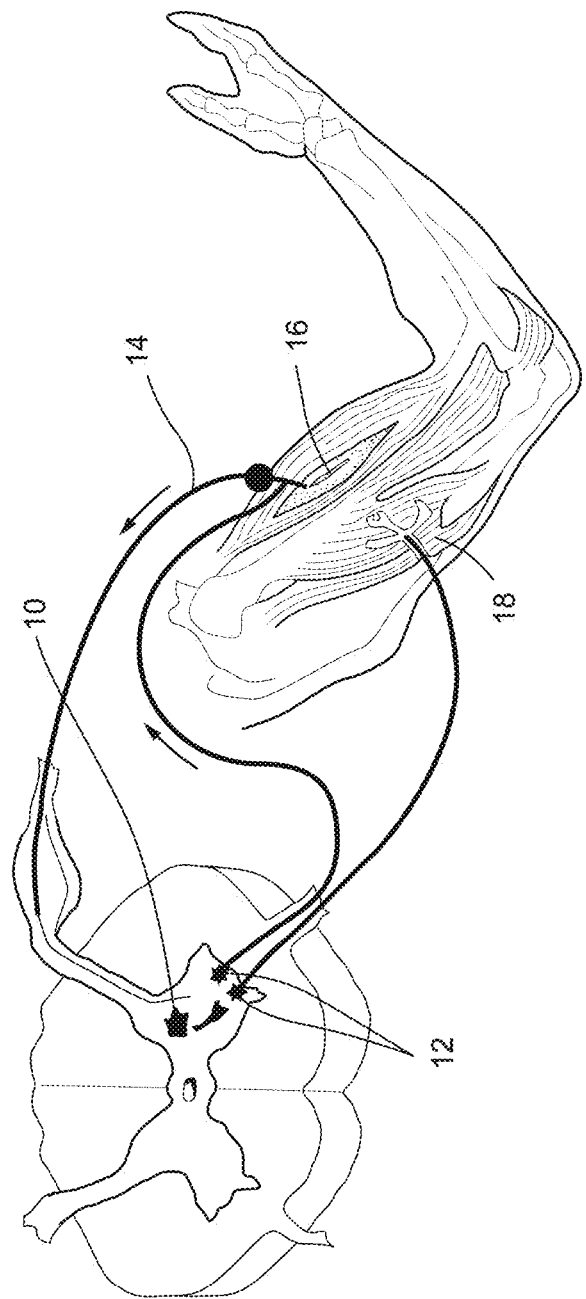

It is highly desirable to provide better operating performance to perform a mission and to prevent catastrophic failures. An ultimate goal is to monitor and manage the integrity of structures in operating conditions during their entire working life. The development of in-service structural health monitoring ("SHM") and self-adapting morphing ("SAM") has attracted a large number of academic and industrial researchers.

Using SHM, once damage is detected during operation of a structural platform, in general, an evaluation process is performed through damage identification to determine whether to continue operation or to stop operation in order to perform structural repair.

Different kinds of damage may occur due to severe operational conditions. For example, damage can be caused by fatigue, erosion, corrosion, impact, moisture and/or other effects. The operational life cycle of a structural platform can be significantly reduced. In some cases, the entire structural component must be replaced instead of being repaired.

Operational loads monitoring ("OLM") can be a part of real operational condition analysis and can provide an estimation of the real usage of the vehicle's structural components. The analysis between real and design loads enables estimation of usage severity, including the determination of extreme events, such as hard-landings, over-speeds, and others.

Known equipment and sensors such as accelerometers can be used to monitor the vertical and normal accelerations in a vehicle. By means of these accelerations measurements, fatigue loads can be estimated to provide data related to remaining structural life. Currently, several operators of vehicles still use such methods to measure the real loads of the vehicle. On the other hand, advances in onboard recorder capabilities now store hundreds of parameters with higher acquisition rates. Such stored data can be used to provide data for more accurate analysis.

Structural integrity monitoring can be done by an indirect method, such as OLM or using direct methods such as damage detection systems. Over the last few years, efforts have been made to investigate damage detection systems applied to structural components of vehicles. Several studies of Structural Health Monitoring (SHM) applications provide analysis showing a significant reduction in life-cycle costs.

Seeking safety improvement, reduction of maintenance cost and human error, efforts are underway to develop automatic SHM systems capable of calculating operational loads and detecting damages in real time without need for human interference or attention. Therefore, new SHM technologies will lead to the use of maintenance plans based on structural condition, and in the future, a prognosis analysis for anticipating early damages.

Inspired by nature, many researchers have dedicated themselves to creating systems and structures that have an adaptive behavior according to the environment. The development of smart structures is a design philosophy that has gained importance in recent years. In general, smart structure systems consist of or comprise sensors and actuators, such as: shape memory alloy, piezoelectric, magnetostrictive, fluids magneto, and others among many possibilities. See e.g., Addington et al., Smart Materials and New Technologies (Architectural Press 2005) and Schwartz, Smart Materials (CRC Press 2009), incorporated herein by reference.

The human body has an amazing ability to react and adapt the muscular system when required to perform a mission. For example, when one's brain commands one's body to lift a glass to the mouth using the hands, the nervous system evaluates the environmental conditions (e.g., the weight of the cup, the distance between the cup and the mouth, how the cup must be grasped to prevent it from spilling, etc.) and activates the muscular system to accomplish the mission (see FIGS. 1A-1D). In the example shown in FIG. 1A, an inhibitory interneuron 10 and associated neural network within the human brain communicates via alpha motor neurons 12 and the spinal cord with muscle spindle 16 and antagonistic muscle 18. Biofeedback (including sensing information) is provided via nerve path 14. As shown in FIGS. 1B-1D, several muscles (e.g., a homonymous muscle 20, a synergist muscle 22 and an antagonist muscle 18) are all involved and work together in movements as simple as passively stretching the arm to fill a cup with liquid and then lift the filled cup to the lips. Such muscles controllably interact with and against one another to achieve fine motor control with desired position, balance, etc.

Researchers have long recognized that birds were able to change their body position in flight in order to perform specific maneuvers or adjust their aerodynamic profile to suit flight conditions. This orientation-adaptive body shaping has been termed 'morphing' in the literature. The words 'transform' and 'morphing' are actually forms of the word 'metamorphosis', which derives from the Greek 'meta' (change) and 'morpheme' (form). That is the description of the capability of birds to change shape or geometry of their bodies and wings for both a heightened maneuverability and a stable flight within multiple environmental conditions (see FIG. 2 showing outstretched wings for landing and bent wings for stable flight). That is the description of the birds' capability to change shape or geometry of their bodies and wings for both a heightened maneuverability and a stable flight by adapting to multiple environmental conditions.

This ability has been studied and often duplicated by aviation engineers, to the extent that it was technologically possible. Thus, observations of birds have inspired in numerous cases technological progress in aircraft design and development.

FIG. 3 shows example types of wings of three different birds. Wings with low elongation (aspect ratio=6.8) such as a pheasant wing, usually allow rapid and slow take-off, but is not useful for gliding. The wings with a 9.3 aspect ratio or elongation (eagle wings) are usually longer and have feathers, which are adjusted as a type of control surface for more precise handling. Wings for waders (not shown), with an elongation ratio of 12.5 are useful for higher speeds and sliding, but not for a quick take-off, because a large amount of energy is needed to train such long wings. Aspect ratio 13.8 lengthening wings of seagulls are usually useful for close sliding surfaces, such as sea and land to take advantage of air currents in order to preserve energy.

In general, "self-adapting morphing" platforms are multifunctional structural platforms that change their external shape substantially with the aid of a stimulus to adapt to a changing of the mission environment during an operation, e.g., providing better operating performance to perform a mission.

This creates a system with superior capabilities not possible without shape changes when compared to conventional structural platforms. The self-adapting morphing can become more competitive for example including more mission tasks or capabilities to the platform.

For example, new design capabilities for future aircraft may require certain aspects of the vehicle configuration (and therefore its structure) to reconfigure during an operational broad range of flight conditions. The example non-limiting technology herein provides an integrated system and method to acquire the health state of a structure, identify the presence of damage or excessive/unusual operational loads, and provide self-adapting morphing can result in flow control and structural shape control leading to breakthroughs in vehicle drag reduction. SHM systems can provide operational loads and/or structural damage information to the self-adapting morphing systems, which can use this data for structural morphing decisions.

Taking a sensory network based on a SHM system (Structural Health Monitoring), the system informs a damage assessment and operational loads with maturity and robustness.

An output of the SHM system includes damage and critical loads characterization including:
Detection
Localization
Quantification of the damage sizing or/and load intensity.

After knowing about the health state of a structure and identifying the presence of damage or excessive/unusual operational loads, a SAM (self-adapting morphing) that may be independent is integrated with the SHM system. The integrated SAM to SHM provides (after finding a damage or event with critical loads), a better operating configuration that will improve the performance to perform a mission.

Like the human nervous system, the SHM system senses the presence of a damage and critical operational loads, and like the human muscular system the SAM performs morphing for a better performance of the mission. In this approach, these systems are independent but integrated, exchanging information (see FIG. 4).

In more detail, referring to FIG. 4, the SHM senses that there is a problem ("Houston, we have a problem"). Such an optimized SHM can provide operational loads and a sensory network that can inform of excessive/unusual loads and damage based on maturity, robustness and/or online assessment. Such an SHM is integrated with a SAM system, which can be independent of the SHM and permit aerospace or other platforms to provide self-adapting morphing of the structural platform through actuators such as: shape memory alloy, piezoelectric, magnetostrictive, fluids magneto, and others. This is similar to how the human body characterizes damage by detection, localizing and quantifying damage (e.g., by sizing and/or intensity) such as detecting injury of the hand and then adapting to the condition.

Therefore, example non-limiting embodiments provide a structural integrity management system providing the integration of a SHM sub-system that continuously evaluates a structural platform. When the system detects damage or critical loads, the system starts a self-adapting morphing sub-system causing a change to the external shape substantially becoming more competitive including more mission tasks or capabilities to fulfill the requirements of this platform (see FIG. 4).

An application example is presented in FIG. 5. Considering as a structural platform an aircraft, it's known in the aviation industry that winglets can improve the fuel efficiency of the aircraft, by reducing the wingtip vortices formed by the difference between the pressure on the upper and lower surfaces of an aircraft's wing.

The angular position of the current fixed winglet is defined choosing the flight conditions that will be prioritized. Normally angles are selected ideal to reducing drag when the aircraft is cruising, but less effective when it is taking off or descending. This is the reason that movable winglets would be a significant improvement to flight efficiency.

Wingtip angular morphing associated with operational loads is an example of the sensory system integration with morphing to increase aircraft flight performance. Once the operational loads monitoring system after data analysis detects a change in the flight mission, then, this system can start the morphing system where it will trigger change of the wingtip in order to modify wing geometries, reducing the aerodynamics effects on the wing and increasing the flight performance (see FIG. 5).

Thus, by using the technology proposed herein, an optimized SHM 202 can provide operational loads and a sensory network can inform the current loads to the SAM system 208, which can be independent of the SHM and allows the winglet to self-adapt the angle to an ideal form and position considering the phase of the flight (take off, cruise, landing, etc.). The SAM 208 induces the winglet to modify the angle to the pre-defined patterns through actuators such as: shape memory alloy, piezoelectric, magnetostrictive, fluids magneto, and others.

After morphing, the SHM sub-system may also perform a reassessment of the structure certifying if the structure is safe for operation (204, 206, see FIG. 6A).

Figure 6B:
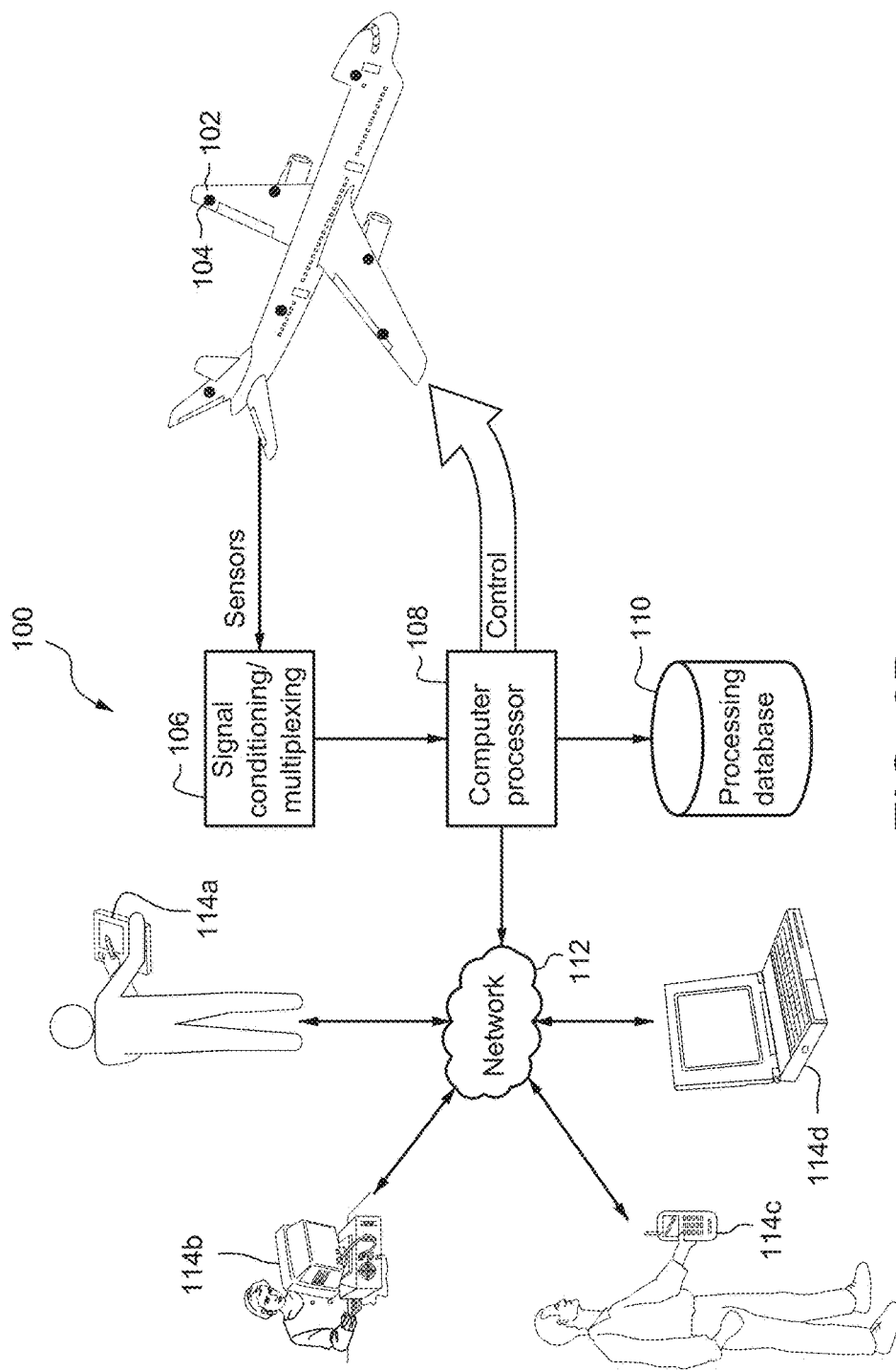
FIG. 6B shows an example hardware and software based processing system for implementing the process of FIG. 6A.

FIG. 6B shows an example overall system 100 that can be used to implement SHM sub-systems 202, 206 and the SAM sub-system 208 shown in FIG. 6A. In the example shown, aircraft 102 has disposed thereon a number of sensors 104 of various types as described above. The outputs of such sensors 104 are fed to a signal conditioning/multiplexing circuit 106, which in turn feed the outputs to a computer processor 108. Computer processor 108 may comprise any number of individual processors such as microprocessors, and embedded processors, ASICs or the like that execute software instructions, firmware instructions or other processes.

The output of computer processor 108 provides control information and commands to morph aircraft 102. Such morphing adaptations could come as described above, comprises as one example reconfiguring the angle of winglets on the aircraft wings 102. Other examples might include deforming certain parts of the fuselage, shifting mass or weight using hydraulic or other automatic mechanisms, operating multiple control surfaces, or the like. Such adaptations can be performed by any of a variety of means including e.g., hydraulics, temperature changes, "smart" materials, geared mechanical reconfigurations, deformable materials and structures, color changes, etc. Such adaptations can change, improve and/or optimize performance based on current environmental conditions as sensed by sensors 104.

In the example shown, computer processor 108 executes software stored in storage device 110 which may also comprise a processing database. Such a processing database may include data and executable code. In one particular example, the processing database 110 including the executable code executed by computer processor 108 may provide neural networks or other artificial intelligence to provide the self-adapted morphing 208 discussed above. In other embodiments, the SHM sub-system 202, 206 and the SAM sub-system 208 may comprise different computers and associated computer systems that communicate with one another in various ways. In one particular embodiment, the SHM sub-system 202, 206 may be on board the aircraft 102 as may the SAM sub-system 208. In other embodiments, the computer processor 108 may communicate in real time via one or more networks 112 with other processing devices 114 including human input in order to more effectively and efficiently provide self-adapting morphing as discussed above.

In the example shown in FIG. 6B, the computer processor 108 automatically detects damage to the structure of the aircraft 102 based on inputs from the sensors 104, automatically calculates operational loads, and automatically determines loads mission profiles and/or extreme operational events including but not limited to hard landings and overspeeds. The computer processor 108 then, in response to such calculated operational loads and based on the load mission profiles and exceptional operational events detection, automatically changes the external shape of the aircraft 102 (e.g., by adapting winglet shape as one example) substantially to provide a self-adapting morphing and to adapt the aircraft to mission environment during flight. In the example embodiment, the computer processor 108 can automatically change the external shape of the aircraft 102 to provide better operating performance for accomplishing the mission and/or to perform more mission tasks or capabilities required by the aircraft.

In this particular example non-limiting embodiment of FIG. 6B, the computer processor 108 implements a structural health monitoring system comprising of a plurality of transducers 104 including a plurality of sensors or pairs of actuators and sensors, with the signal conditioning/multiplexing device 106 interrogating at least one of said sensors 104 to produce and obtain signals. The computer processor 108 receives such sensor signals via the signal conditioning/multiplexing device 106 and performs analyses for damage identification. In this example embodiment, the computer processor 108 further provides an operational loads monitoring system that implements parametric models using parameter data capable of providing an estimation of the real usage of the aircraft 102's structural components and to identify extreme operational events. The parameter data may include for example acceleration, strain, stress, load, vibration, resonance, position and/or temperature or any combinations thereof. Such parametric models may be stored for example in the processing database 110.

In the non-limiting embodiment shown in FIG. 6B, the computer processor 108 further implements a self-adapting morphing system comprising mechanical or electrical devices with or without the use of smart materials with the ability to realize a flexible control of the geometry of the aircraft 102. In the particular example shown, the computer processor 108 may integrate the structural health monitoring system and the self-adapting morphing system with the unique or distinct network of sensors and/or actuators. In one example embodiment, the integrated system including the structural health monitoring system and the self-adapting morphing system may be exclusively one box control. In other embodiments, the integrated system may be with box control separated for the structural health monitoring and the self-adapting morphing system.

The sensors 104 may comprise fiber optics sensors or piezoelectric sensors or polymer sensors. The structural health monitoring performed by computer processor 108 may use Lamb waves or electromechanical impedance or fiber Bragg gratings or acoustic emission or vacuum or any other variety of sensor inputs. The network sensors may be embedded in the structure or not embedded in the structure of aircraft 102. As mentioned above, the self-adapting morphing system may use shape memory alloy, piezoelectric, magnetostrictive and/or magneto fluid controls to adapt or change shape.

Figure 7:
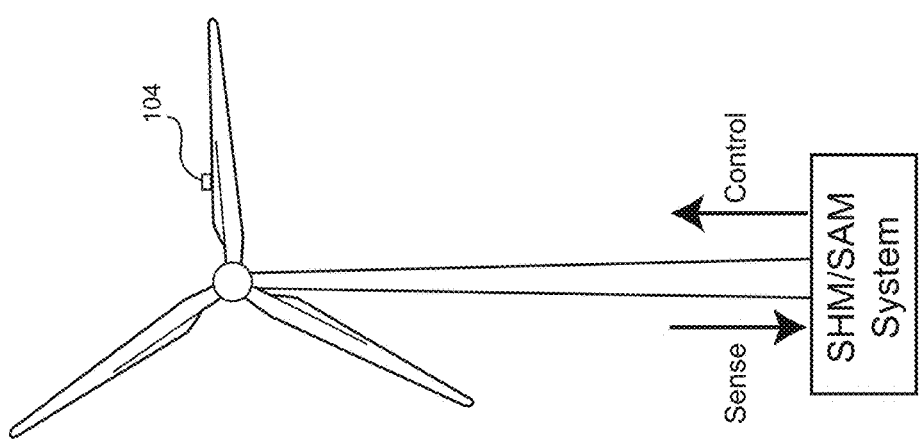
FIG. 7 shows an example wind turbine application.

FIG. 7 shows another example application. In this application, wind turbine blades are subject to several types of impacts, often caused by birds striking the blades. Some bird strikes could create severe damage and lead to a catastrophic failure, jeopardizing the whole turbine structure and in some cases human lives. In a further embodiment, upon an impact being detected or sometime after an impact, the detection system determines damage, and performs analysis to determine localization and quantification (sizing or/and intensity)

of the damage. Then, this system can start the morphing system to change the geometric configuration of the trailing edges of turbine blades, in order to reduce the loads on the damaged area, avoiding catastrophic failure and extending the operation on the wind turbine operation.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method to assess the condition and self-adapting morphing of a structural platform, comprising:
   automatically by computer, detecting damage to a structure;
   automatically by computer, performing analysis to determine localization and sizing or/and intensity quantification of the detected damage;
   automatically by computer, calculating operational loads of the structure;
   automatically by computer, determining at least one of loading mission profiles and extreme operational events including hard-landings and over-speeds sustained by the structure;
   automatically by computer, determining a self-adapting morphed geometric configuration for the structure to adapt the structure to (a) a mission, (b) the determined localization and sizing or/and intensity quantification of the detected damage, (c) calculated operational loads, and (d) at least one of determined loading mission profiles and extreme operational events during operation of the structure, and
   automatically adaptively morphing the geometric configuration of the structure based on the determined morphed external shape to dynamically reconfigure the external shape and geometric configuration of the structure in response to changing operational flight conditions and the determined localization and sizing or/and intensity quantification of the detected damage.

2. An integrated system for assessing the condition of and self-adapting morphing of a structural platform comprising:
   a Structural Health Monitoring System (SHM) comprising a plurality of transducers, including a plurality of sensors or pairs of actuators and sensors, a device to interrogate at least one of said sensors to produce signals, and a processor device to receive the signals and perform analyses for damage identification, the Structural Health Monitoring System being configured to automatically determine localization and sizing or/and intensity quantification of the detected damage;
   an Operational loads Monitoring System (OLM) comprising parametric models using parameter data capable of providing an estimation of the real usage of the vehicle's structural components and identifying extreme operational events;
   a Self-Adapting Morphing System (SAM) comprising mechanical or electrical devices with or without the use of smart materials with the ability to realize a flexible control of the geometry of the structural platform, the Self-Adapting Morphing System comprising at least one processor that dynamically reconfigures the structural geometry of the structural platform in response to changing operational flight conditions and the determined localization and sizing or/and intensity quantification of the detected damage; and connections to integrate the SHM system and the SAM system with a unique or distinct network of sensors/actuators, wherein:
   the integrated system (SHM+SAM) is exclusively one box control; or
   the integrated system (SHM+SAM) has box control separated for SHM and SAM.

3. The system according to claim 2, wherein the sensors comprise fiber optics sensors or piezoelectric sensors or polymer sensors.

4. The system according to claim 2, wherein the structural health monitoring uses Lamb waves or electromechanical impedance or fiber Bragg gratings or acoustic emission or vacuum.

5. The system according to claim 2, wherein the sensors are embedded in the structure.

6. The system according to claim 2, wherein the Self-Adapting Morphing system uses at least one of shape memory alloy, piezoelectric, magnetostrictive, and magneto fluids.

7. The system according to claim 2, wherein the Operational Loads Monitoring System uses parameter data including at least one of acceleration, strain, stress, load, position, and temperature.

8. The system according to claim 2, wherein the sensors are not embedded in the structure.

9. The method of claim 1 wherein the computer determines loading mission profiles.

10. The method of claim 1 wherein the computer determines extreme operational events including hard-landings and over-speeds sustained by the structure.

11. The method of claim 1 wherein the structure includes a wing having a wingtip, and the computer morphs wing geometries to reduce the aerodynamics effects on the wing and increase flight performance.

12. The system of claim 2 wherein the structural platform includes a wing having a wingtip, and the Self-Adapting Morphing System triggers morphing change of the wingtip in order to modify wing geometries in response to detected damage, reducing the aerodynamics effects on the wing and increasing flight performance.

13. The method of claim 1 wherein the computer self-adapts the structure to an ideal or more optimal form and position for a phase of flight including at least one of take off, cruising and landing.

14. The system of claim 2 wherein the Self-Adapting Morphing System self-adapts the structural platform to an ideal or more optimal form and position for the phase of flight including at least one of take off, cruising and landing.

15. The method of claim 1 wherein the structure includes a winglet and the computer self-adapts the angle of the winglet to an ideal form and position considering a phase of flight.

16. The system of claim 2 wherein the structural platform includes a winglet and the Self-Adapting Morphing System self-adapts the angle of the winglet to an ideal form and position considering the phase of flight.

17. The method of claim 1 wherein the computer performs a reassessment of the structure after morphing certifying if the morphed structure is safe for operation.

18. The system of claim 2 wherein the Self-Adapting Morphing System performs a reassessment of the structural platform after morphing certifying if the morphed structural platform is safe for operation.

19. The method of claim 1 wherein the adaptive morphing includes at least one of deforming certain parts of a fuselage, shifting mass or weight using hydraulic or other automatic mechanisms, and operating multiple control surfaces.

20. An aircraft having an airfoil and comprising:
sensors disposed on the aircraft;
at least one processor operatively coupled to the sensors, the at least one processor determining changed operational conditions of the aircraft including localization and sizing or/and intensity quantification of structural damage and extreme operational events, the at least one processor being programmed to track current flight phase; and
an arrangement operatively coupled to the at least one processor and the airfoil, the arrangement comprising:
at least one of mechanical and electrical devices connected to or part of the airfoil, the at least one of mechanical and electrical devices being structured to morph the shape and geometry of the airfoil to thereby change its performance; and
the same or different at least one processor operatively connected to the at least one of mechanical and electrical devices, the same or different at least one processor being configured to control the at least one of mechanical and electrical devices to dynamically and controllably morph the geometric configuration of the airfoil in response to the determined changed operational conditions and current flight phase and the determined localization and sizing or/and intensity quantification of the detected damage to thereby dynamically reconfigure and adapt the geometric configuration of the airfoil to changing operational flight conditions and the determined localization and sizing or/and intensity quantification of the detected damage, the same or different at least one processor being further configured to assess whether the dynamically morphed surface is safe for operation.

* * * * *